United States Patent [19]

Stouffer et al.

[11] 4,099,420
[45] Jul. 11, 1978

[54] TRANSDUCER POSITIONING APPARATUS

[75] Inventors: James R. Stouffer, Ithaca, N.Y.;
Rudy G. Westervelt, Florissant, Mo.

[73] Assignee: Cornell Research Foundation, Inc., Ithaca, N.Y.

[21] Appl. No.: 803,260

[22] Filed: Jun. 3, 1977

[51] Int. Cl.² ............................................. G01N 29/00
[52] U.S. Cl. ............................................................ 73/629
[58] Field of Search .............. 73/67.8 R, 67.8 S, 67.7, 73/67.5 R, 71.5 US, 627, 628, 629, 618, 620, 625

[56] References Cited

U.S. PATENT DOCUMENTS

| 3,165,923 | 1/1965 | Lund | 73/67.8 R |
| 3,496,764 | 2/1970 | Stouffer | 73/67.8 S |
| 3,603,303 | 9/1971 | Stouffer | 73/67.8 S |
| 3,722,263 | 3/1973 | Hautaniemi et al. | 73/67.8 S |
| 4,027,528 | 6/1977 | Tyree | 73/67.8 S |

*Primary Examiner*—Richard C. Queisser
*Assistant Examiner*—Stephen A. Kreitman
*Attorney, Agent, or Firm*—Lawrence E. Laubscher; Ralph R. Barnard; Theodore C. Wood

[57] ABSTRACT

A transducer positioning apparatus is disclosed which includes telescoping frame sections, together with pivotally adjustable gimbal supports for accurately mounting a plurality of transducers upon the skin side of a suspended animal carcass, respectively, whereby fat thickness, lean depth and external carcass length are measured by the transducers in conjunction with conventional ultrasonic imaging equipment.

7 Claims, 5 Drawing Figures

TRANSDUCER POSITIONING APPARATUS

BRIEF DESCRIPTION OF THE PRIOR ART

Sonic inspection apparatus for inspecting animal carcasses such as hogs, for usable meat value are well known in the patented prior art, as evidenced by the inventor's prior U.S. Pat. No. 3,496,764 and the patents to Lund U.S. Pat No. 3,165,923, McDicken U.S. Pat. No. 3,688,564 and Hautaniemi et al U.S. Pat. No. 3,722,263. The use of a couplant liquid in connection with the sonic transducer means to prevent the loss of sonic energy and thereby improve the accuracy of measurement is disclosed in the inventor's prior U.S. Pat. No. 3,603,303. It has been further proposed to utilize computer means in connection with various types of measuring transducers to automatically grade the carcass for meat content, as evidenced, for example, by the patents to Kennedy U.S. Pat. No. 3,916,484, Sourby et al U.S. Pat. No. 3,940,998 and Sumption et al U.S. Pat. No. 3,979,835 and the articles "Electronics Boost Profit Potential for Pork Cut," *The National Provisioner*, Aug. 16, 1975 (pages 14–18, 20, 24, 25) and "Computerized Hog Cut", *Meat Industry*, September, 1975 (pages 27–32).

The known carcass measuring and inspecting systems have the inherent drawback that it is difficult to quickly mount and accurately position the transducer devices on carcasses of various sizes. The present invention was developed to avoid the above and other drawbacks of the known carcass inspecting apparatus.

SUMMARY OF THE INVENTION

The primary object of the subject invention is to provide improved transducer positioning apparatus for quickly and properly aligning several transducers simultaneously upon the skin side of a warm or chilled suspended animal carcass to obtain readings of fat thickness and lean depth in conjunction with ultrasonic imaging equipment. A telescopic frame is provided which is adapted for attachment to the suspended carcass, a plurality of transducers being connected with the frame by gimbal support means to insure proper contact between the transducer face and the skin of the carcass. In order to assure proper contact, a liquid couplant is extruded at the transducer face just prior to contact with the carcass.

Another object of the invention is to provide means for simultaneously determining the external carcass length.

BRIEF DESCRIPTION OF THE FIGURES

Other objects and advantages of the invention will become apparent from a study of the following specification when viewed in the light of the accompanying drawing, in which.

DETAILED DESCRIPTION

Figure 1:
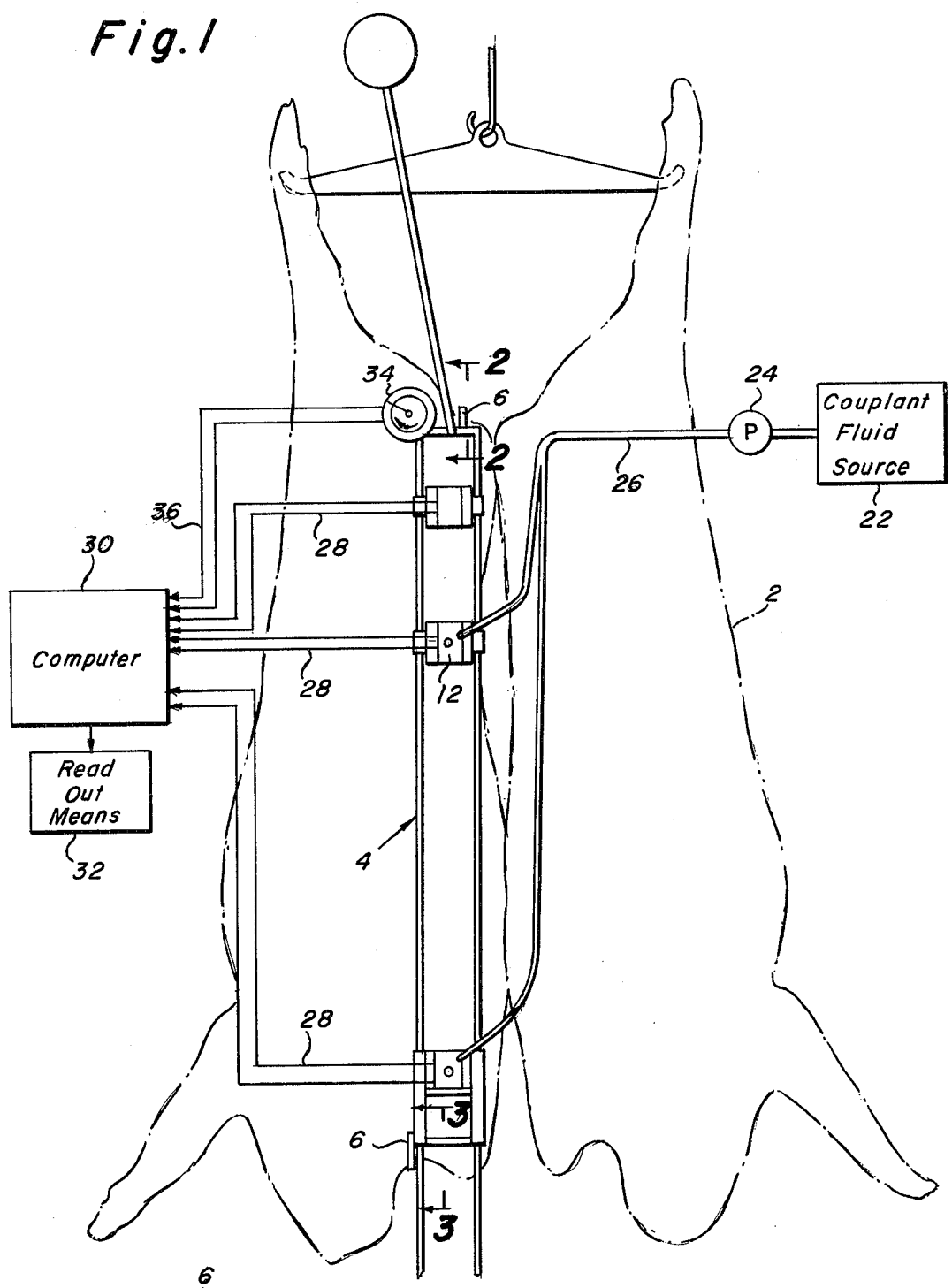
FIG. 1 is a diagrammatic illustration of the transducer positioning apparatus mounted upon an animal carcass.
Figure 2:
FIGS. 2 and 3 are detailed sectional views taken along lines 2—2 and 3—3 of FIG. 1, respectively.
Figure 3:
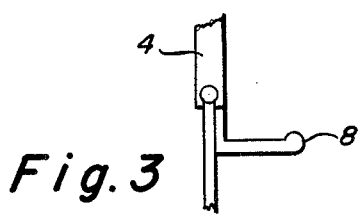
Figure 4:
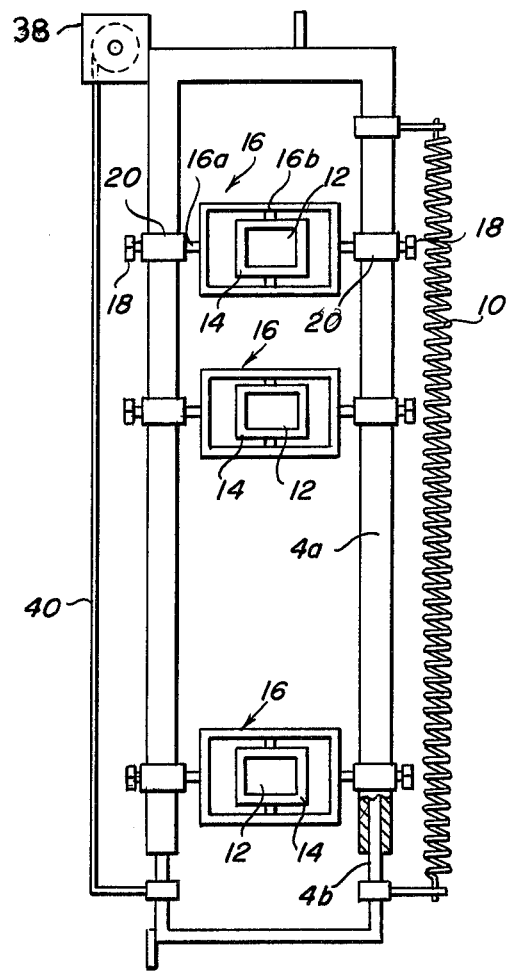
FIG. 4 is an elevational view of the transducer mounting apparatus.

Referring first more particularly to FIGS. 1–4, the improved apparatus for positioning conventional ultrasonic transducers upon the skin side of an animal carcass 2 (such as a hog carcass) includes vertically arranged telescoping frame means 4 having at its upper end a first hook 6 for hanging one end of the frame above the tail portion of the carcass, and a second hook 8 at its lower end for indexing the other end of the frame at the notch in the jowl-shoulder junction where the head has been removed. Spring means 10 bias the telescoping frame sections 4a and 4b toward their retracted positions, respectively, and enable the frame 4 to be expanded or retracted for mounting on a wide variety of carcass lengths.

A plurality of vertically spaced sonic transducers 12 are provided, each of which includes a support block 14 that is connected with the frame 4 by gimbal means 16 having two orthogonally arranged pivot axes 16a and 16b, respectively, thereby to insure proper contact between the transducer mounting block 14 and the skin of the carcass. Set screws 18 and mounting sleeves 20 permit the transducer gimbal support means 16 to be vertically adjusted relative to the frame 4 for proper positioning of the transducers upon the carcass.

Figure 5:
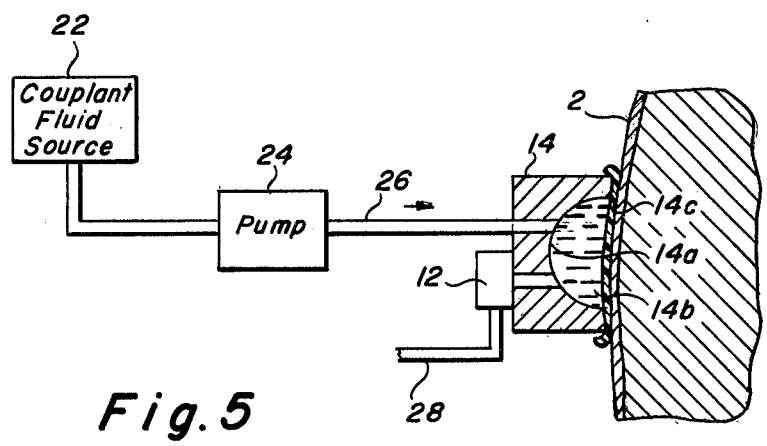
FIG. 5 illustrates somewhat diagrammatically in detailed cross section a transducer positioned upon the carcass, and the associated source of couplant fluid.

As shown in FIG. 5, couplant fluid source 22 is connected to transducer 12 by hose means 26. Just prior to contact with the carcass, couplant fluid is pumped by pump means 24 via hose means 26 to the face of transducer 12.

Signals are transmitted from the transducers 12 via conductors 28 to conventional computer means 30 from which the measured data is displayed on read-out means 32, as is known in the art.

As shown in FIG. 1, carcass length measuring means 34 are provided which include sensors attached to frame 4 for determining carcass length from the jowl-shoulder junction along the midline of back to tail. Signal transmitting means 36 connect the measuring means to computer means 30. In an alternative embodiment shown in FIG. 4, the external measuring means 38 comprises a holder 38 for a conventional measuring tape 40.

OPERATION

When the apparatus above described is to be mounted upon a suspended animal carcass 2, pump means 24 is activated to pump couplant fluid from source 22 via hose means 26 to transducer block chamber 14b. In the preferred embodiment of the invention, three sonic transducers 12 are slidably connected with the frame 4 for positioning along the midline of the carcass for fat thickness readings at the first rib, last rib and last lumbar vertebra, respectively, as well as laterally over the shoulder and ham for fat thickness and muscle depth readings. Additional transducers may be added to the frame to give readings at other locations, if desired.

The upper hook 6 on frame 4 is attached to the tail portion of the carcass 2, whereupon the telescoping frame 4 is expanded downwardly against the biasing force of spring means 10, whereupon the second hook means 8 is attached at the jowl-shoulder junction. Owing to the gimbal support means 16 for each transducer block 14, proper contact between transducer block face 14c and the skin of the carcass 2 is ensured. As the transducer block face 14c is positioned upon the skin of the carcass, sonic pulses are transmitted into the animal tissue, and the reflected signals are sent via signal conductors 28 to the computer means 30 and read-out means 32. Simultaneous signals are transmitted from the electronic measuring means 34 to the computer means 30 and read-out means 32 via signal conductors 36.

Once the desired measurements have been indicated by the read-out means, the apparatus may be quickly and easily removed and placed on another suspended carcass. In this manner, fat, muscle depth and external length measurements may be rapidly and accurately determined for a plurality of animal carcasses.

While, in accordance with the provisions of the Patent Statutes, the preferred embodiment of the invention has been illustrated and described, it will be apparent to those skilled in the art that changes may be made without deviating from the inventive concepts set forth above.

What is claimed is:

1. In an ultrasonic carcass inspection apparatus including at least one sonic transducer for inspecting an animal carcass that is supported by its hind legs, the improvement which comprises vertical frame means for mounting the sonic transducer adjacent the skin side of the carcass, said frame means including (a) a pair of telescopically connected sections that are relatively vertically slidably displaceable between expanded and retracted positions, respectively;

(b) spring means biasing said frame sections toward their retracted positions, respectively;

(c) means for mounting the sonic transducer on one of said sections;

(d) first hook means for connecting one of said frame sections with the tail portion of the carcass; and (e) second hook means for connecting the other of said frame sections with the jowl-shoulder junction of the carcass.

2. Apparatus as defined in claim 1, and further including means connected between the opposite ends of said sections for measuring the length of the animal carcass.

3. Apparatus as defind in claim 1, wherein said transducer mounting means includes gimbal means connecting the transducer with said frame for movement about two orthongonally arranged pivot axes.

4. Apparatus as defined in claim 3, wherein a plurality of sonic transducers are each connected by gimbal means with said one frame section, said sonic transducers being arranged in vertically spaced relation on said frame section for obtaining readings at the first rib, last rib and last lumbar vertebra portions of the carcass, respectively.

5. Apparatus as defined in claim 4, and further including means for supplying a couplant fluid between the face of each sonic transducer and the skin of the carcass.

6. Apparatus as defined in claim 4. wherein said sections are coplanar.

7. Apparatus as defined in claim 4 and further including means for vertically adjustably positioning each of said gimbal means on said frame section, respectively.

* * * * *